US005772652A

United States Patent [19]

Zielinski

[11] Patent Number: 5,772,652

[45] Date of Patent: Jun. 30, 1998

[54] STAB CAP FOR A VIAL HAVING A PUNCTURABLE SEAL

[75] Inventor: Peter M. Zielinski, Milleville, N.J.

[73] Assignee: Comar, Inc., Buena, N.J.

[21] Appl. No.: 827,989

[22] Filed: May 14, 1997

[51] Int. Cl.$^6$ .......... A61B 19/00; D65D 39/00

[52] U.S. Cl. .......... 604/411; 604/415; 604/403; 215/247; 215/DIG. 3

[58] Field of Search .......... 604/411, 412, 604/415, 403; 215/247–249, 297, 321, DIG. 3

[56] References Cited

U.S. PATENT DOCUMENTS

| | | | |
|---|---|---|---|
| 2,289,677 | 7/1942 | Perelson . | |
| 2,326,490 | 8/1943 | Perelson . | |
| 2,342,215 | 2/1944 | Perelson . | |
| 2,653,609 | 9/1953 | Smith | 604/415 |
| 3,940,003 | 2/1976 | Larson | 604/411 |
| 3,977,555 | 8/1976 | Larson . | |
| 4,128,098 | 12/1978 | Bloom et al. . | |
| 4,589,879 | 5/1986 | Pearson | 604/411 |
| 4,883,483 | 11/1989 | Lindmayer . | |
| 5,279,576 | 1/1994 | Loo et la. . | |

*Primary Examiner*—John G. Weiss
*Assistant Examiner*—Dennis Ruhl
*Attorney, Agent, or Firm*—Brady, O'Boyle & Gates

[57] ABSTRACT

A stab cap for a vial wherein an open-ended sleeve functions not only as a closure for sealing against a seal disc on the open end of a vial but also as a support for a tubular member having a depending tubular portion terminating in a sharp end portion for puncturing the seal disc to facilitate the transfer of fluid from the vial to a syringe. A flexural connection is provided between the sleeve and tubular member, the connection being integral with the tubular member and formed of the same material.

7 Claims, 2 Drawing Sheets

STAB CAP FOR A VIAL HAVING A PUNCTURABLE SEAL

BACKGROUND OF THE INVENTION

Various stab devices have been provided for puncturing a seal on the open end of a medicant container, such as a vials for transferring a fluid from the vial to a syringe barrel, prior to attaching a syringe needle to the barrel for injection of the fluid into a patient.

U.S. Pat. Nos. 2,289,677; 2,326,490; and 2,342,215 disclose stab devices mounted on a vial stopper, so that the stopper not only functions as a closure for the vial, but also as a carrier for the needle which punctures the vial seal. While these devices are satisfactory for their intended purposes they are characterized by certain disadvantages in that the flexural connection of the puncturing needle to the stopper is formed of a different material from the needle which results in an expensive stab device both in material and labor.

Other stab devices have been proposed which are adapters attachable to a vial but are not constructed and arranged to also function as a closure seal for the vial.

After considerable research and experimentation, the stab cap of the present invention has been devised wherein an open-ended sleeve functions not only as a closure seal for the vial, but also as a carrier for the puncture needle and having a flexural connection between the sleeve and puncture needle of the same material as the needle, to thereby reduce the cost for fabricating the stab cap.

SUMMARY OF THE INVENTION

The stab cap of the present invention comprises, essentially, an open-ended sleeve mounted on the end of a vial having a puncturable sealing disc sealing the open end thereof. A tubular member having a depending tubular portion terminating in a sharp end portion is positioned in the sleeve coaxial therewith, and a flexural connection extends between the inner surface of the sleeve and outer surface of the tubular member, whereby the tubular member can be pushed downwardly relative to the sleeve, so that the sharp end portion punctures the seal disc.

The flexural connection is fabricated from the same material as the tubular member and is molded integral therewith.

The stab cap of the present invention functions not only as a closure seal for the vial, but also as a carrier for the puncturing sharp end portion.

DESCRIPTION OF THE PREFERRED EMBODIMENTS

Figure 1:
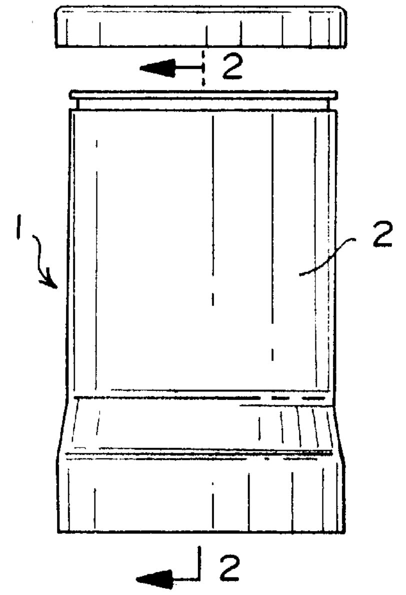
FIG. 1 is a side elevational view of the stab cap of the present invention and associated closure.
Figure 2:
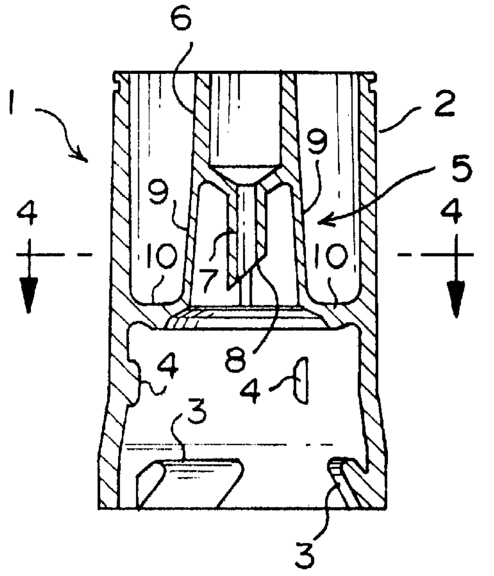
FIG. 2 is a sectional side elevational view of one embodiment of the stab cap.
Figure 3:
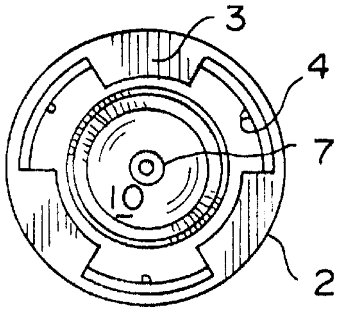
FIG. 3 is a bottom plan view of the cap shown in FIG. 2.
Figure 4:
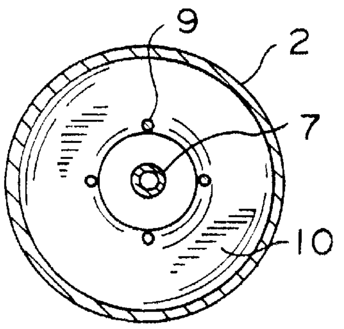
FIG. 4 is a view taken along line 4—4 of FIG. 2.
Figure 5:
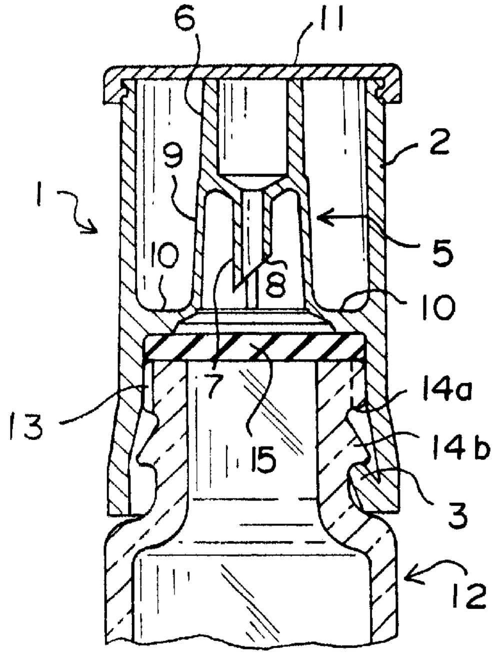
FIG. 5 is a sectional side elevational view showing the stab cap of FIG. 2 and associated closure, mounted on a vial having a puncturable seal.

Referring to the drawings and, more particularly to FIGS. 1, 2, and 5, the stab cap 1 of the present invention comprises an open-ended cylindrical sleeve 2 having a plurality of inwardly extending, upwardly inclined, flexible tabs 3 on the lower end thereof, and a plurality of radially inwardly extending ribs 4 integral with the inner wall surface of the sleeve 2. The upper end of the sleeve is provided with a stab member 5 positioned coaxially with the sleeve 2. The stab member 5 comprises a cylindrical tubular body member 6 having a depending downwardly extending tube or portion 7 having a sharpened lower end 8, forming a puncture needle.

The stab member 5 is supported within the sleeve 2 by a plurality of flexible fingers 9 integral with the tubular body member 6 and an annular wall 10, which is integral with and extends radially inwardly from the inner wall surface of the sleeve 2.

A removable closure is adapted to be snapped onto the upper end of the sleeve to prevent dust and dirt from entering the sleeve 2.

The stab cap 1 of the present invention is part of an overcap assembly for a gear finish vial 12, as shown in FIG. 5 and disclosed in U.S. pending patent application Ser. No. 08/713,028 filed Sep. 12, 1996, owned by the same assignee as the instant application, the disclosure of which is incorporated herein by reference. The neck of the vial 12 has a gear finish 13 and shoulder portions 14*a* and 14*b*. To support the stab cap 1 on the vial 12, during a lyophilization procedure, a pierceable sealing disc 15 is placed in the sleeve 2 between the ribs 4 and annular wall 10. The stab cap 2 is then pressed downwardly onto the vial 12 until the resilient tabs 3 engage under the shoulder portion 14*a*. After the lyophilization procedure, the stab cap 2 is then pressed downwardly until the tabs 3 engage under the shoulder 14*b*, and the ribs 4 become inserted in the space between adjacent teeth in the gear finish 13, whereby the stab cap 1 is sealingly mounted on the vial 12, and prevented from turning relative to the vial.

Figure 6:
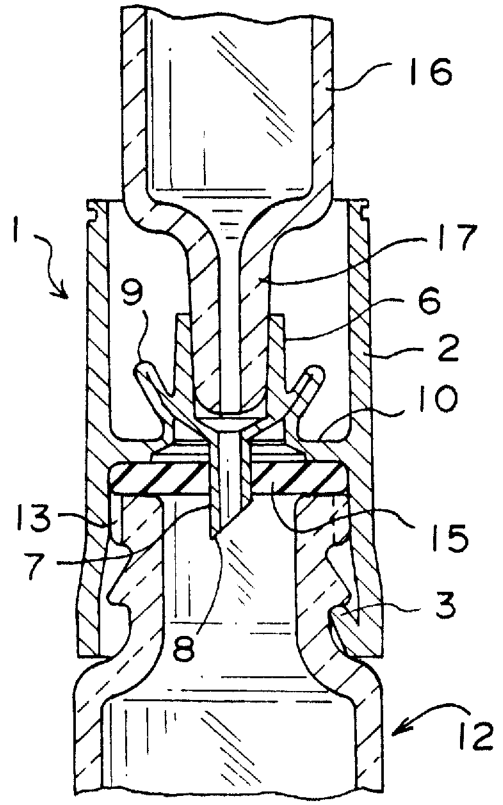
FIG. 6 is a sectional side elevational view showing the operation of the stab cap for transferring fluid from the vial to a syringe barrel.

The operation of the stab cap 1 is illustrated in FIG. 6, wherein the dust closure 1 is reopened and a syringe barrel 16, having a hub portion 17, is inserted into the open end of the sleeve 2 with the hub portion 17 inserted into the tubular body member 6. The syringe barrel 16 is forced downwardly causing the fingers 9 to fold back on themselves, thereby allowing the sharpened end 8 to puncture the disc 15. The syringe barrel 16 is then filled with fluid from the vial, and a sterilized needle is then connected to the hub portion 17 for injection of the medicant into a patient.

Figure 7:
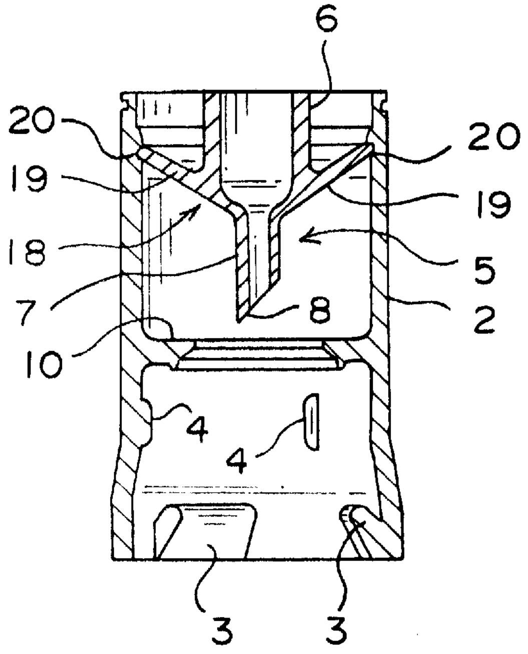
FIG. 7 is a sectional side elevational view of another embodiment of the stab cap of the present invention.
Figure 8:
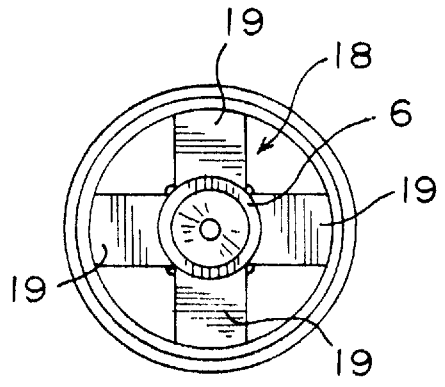
FIG. 8 is a top plan view of the stab cap shown in FIG. 7.
Figure 9:
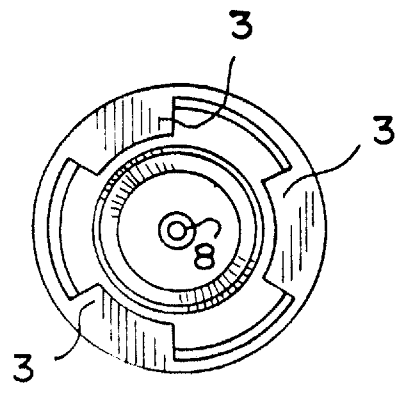
FIG. 9 is a bottom plan view of the stab cap shown in FIG. 7.

While the stab cap 5 shown in FIGS. 2 to 6 is integrally connected to the inner surface of the sidewall of sleeve 2 by fingers 9, FIGS. 7 to 9 disclose another embodiment wherein the stab cap 1 consists of two parts, namely, the sleeve 2 and the stab member 5 supported coaxially within the sleeve 2 by a spider spring 18, having a plurality of radially extending legs 19, having their inner ends integral with the outer wall surface of the tubular member 6 and their outer ends snap-fit into a groove 20 provided in the inner surface of the sleeve 2.

The operation of the stab cap 2 shown in FIGS. 7 to 9 is similar to that of FIG. 6; however, when the hub 17 of the syringe barrel 16 is inserted into the tubular member 6 and then pushed downwardly, the outer ends of the spider spring legs 19 are pulled out of the groove 20, and the entire stab cap 5 slides downwardly in the sleeve 2 to puncture the disc seal 15.

The annular wall 10 shown in the embodiment of FIGS. 1 to 6 and the radially extending legs 19 of the spider spring 18 shown in the embodiment of FIGS. 7 to 9 provide flexural connections between the interior surface of the sleeve 2 and the tubular body member 6. The flexural connections are integral with the tubular body member 6 and fabricated of the same material, such as plastic as the tubular body member 6, depending tubular portion 7, and sharpened end 8, whereby the stab members 5 can be molded as a single component.

From the above description, it will be readily appreciated by those skilled in the art that the stab cap of the present invention is an improvement over previously employed stab caps in that the open-ended sleeve 2 functions not only as a closure seal for the vial 12, but also as a carrier for the stab member 5, and by having the flexural connections 10 and 19 integral with and of the same material as the puncture needle 7, the stab member 5 can be molded as a one-piece component thereby reducing the expense in time and money to fabricate the stab cap.

It is to be understood that the form of the invention herewith shown and described is to be taken as a preferred example of the same, and that various changes in the shape, size, and arrangement of parts may be resorted to, without departing from, the spirit of the invention or scope of the subjoined claims.

I claim:

1. The combination of a stab cap and a vial having a puncturable seal, said stab cap comprising an open-ended sleeve, a transverse annular wall integral with the interior surface of the sleeve dividing the sleeve into an upper portion and a lower portion, a tubular body member positioned in the upper portion of the sleeve and coaxial therewith, an integral depending tubular portion extending downwardly from the tubular body member, said depending tubular portion terminating in a sharp end portion, a plurality of flexible fingers having opposite end portions integral with tubular body member and the annular wall, a plurality of upwardly inclined flexible tabs integral with the open-ended sleeve at the lower end thereof; a vial having an open neck portion, at least one shoulder having an under surface provided on said neck portion, the inclined flexible tabs engaging the under surface of said shoulder, a puncturable seal having an upper surface and a lower surface, the lower surface of the seal being mounted on the open end of said vial, the annular wall in said sleeve engaging the upper surface of said seal, whereby when a hub of a syringe barrel is inserted into the tubular body member and pushed downwardly, the flexible fingers fold back on themselves to thereby allow the tubular body member to move downwardly relative to the open-ended sleeve, thereby causing the sharp end portion to puncture the seal.

2. The combination according to claim 1, wherein the neck of the vial has a gear finish, comprising a plurality of circumferentially spaced gear teeth, a plurality of radially inwardly extending ribs integral with the inner surface of the open-ended sleeve wall in the lower portion thereof, said ribs inserted into the spaces between adjacent teeth of said gear finish, to thereby prevent the stab cap from turning relative to the vial.

3. The combination according to claim 2 wherein a pair of axially spaced shoulders are provided on the vial neck, the flexible tabs engaging one of the axially spaced shoulders of the vial for holding the open-ended sleeve in a nonsealing position above the open neck of the vial during a lyophilization procedure, the flexible tabs engaging the other axially spaced shoulder of the vial for holding the open-ended sleeve in a sealing position on the vial.

4. The combination according to claim 3, wherein the puncturable seal comprises a disc, said disc being supported by said ribs during the lyophilization procedure.

5. The combination of a stab cap and a vial having a puncturable seal, said stab cap comprising an open-ended sleeve, a transverse annular wall integral with the interior surface of the sleeve dividing the sleeve into an upper portion and a lower portion, a tubular body member positioned in the upper portion of the sleeve and coaxial therewith, an integral depending tubular portion extending downwardly from the tubular body member, said depending tubular portion terminating in a sharp end portion, a spider spring having a plurality of radially extending legs having inner ends and outer ends, the inner ends of said legs being integral with the tubular body member, the outer ends of said legs frictionally engaging the inner surface of said open-ended sleeve, a plurality of upwardly inclined flexible tabs integral with the open-ended sleeve at the lower end thereof, a vial having an open neck portion, at least one shoulder having an outer surface provided on said neck portion, the inclined flexible tabs engaging the under surface of said shoulder, a puncturable seal having an upper surface and a lower surface, the lower surface of the seal being mounted on the open end of said vial, the annular wall in said sleeve engaging the upper surface of said seal, whereby when a hub of a syringe is inserted into the tubular body member and pushed downwardly, the outer ends of the spider spring legs slide downwardly on the inner surface of the open-ended sleeve, to thereby allow the tubular body member to move downwardly relative to the open-ended sleeve, thereby causing the sharp end portion to puncture the seal.

6. The combination according to claim 5, wherein a groove is provided on the inner surface of said open-ended sleeve, the outer ends of the spider spring legs being snap fit into said groove.

7. The combination of a stab cap and a vial having a puncturable seal, said stab cap comprising an open-ended sleeve, a transverse annular wall integral with the interior surface of the sleeve dividing the sleeve into an upper portion and a lower portion, a tubular body member positioned in the upper portion of the sleeve and coaxial therewith, an integral depending tubular portion extending downwardly from the tubular body member, said depending tubular portion terminating in a sharp end portion, means operatively connected between the inner surface of the open-ended sleeve and the tubular body member for movably connecting the tubular body member relative to the sleeve, a plurality of upwardly inclined flexible tabs integral with the open-ended sleeve at the lower end thereof; a vial having an open neck portion, at least one shoulder having an under surface provided on said neck portion, the inclined flexible tabs engaging the under surface of said shoulder, a gear finish provided on said neck portion, said gear finish comprising a plurality of circumferentially spaced gear teeth, a plurality of radially inwardly extending ribs integral with the inner surface of the open-ended sleeve wall in the lower portion thereof, said ribs inserted into the spaces between adjacent teeth of said gear finish, to thereby prevent the stab cap from turning relative to the vial; a puncturable seal having an upper surface and a lower surface, the lower surface of the seal being mounted on the open end of said vial, the annular wall in said sleeve engaging the upper surface of said seal, whereby when a hub of a syringe barrel is inserted into the tubular body member and pushed downwardly, the tubular body member moves downwardly relative to the open-ended sleeve, thereby causing the sharp end portion to puncture the seal.

* * * * *